(12) United States Patent
Tillotson (10) Patent No.: US 9,503,696 B2
(45) Date of Patent: Nov. 22, 2016

(54) VISUAL DETECTION OF VOLCANIC PLUMES

(71) Applicant: The Boeing Company, Chicago, IL (US)

(72) Inventor: Brian J. Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 365 days.

(21) Appl. No.: 14/081,356

(22) Filed: Nov. 15, 2013

(65) Prior Publication Data
US 2015/0138355 A1    May 21, 2015

(51) Int. Cl.
| | |
|---|---|
| H04N 7/18 | (2006.01) |
| B64D 47/08 | (2006.01) |
| B64D 45/00 | (2006.01) |
| G01N 21/21 | (2006.01) |
| G01N 21/41 | (2006.01) |
| G01N 21/59 | (2006.01) |
| G01N 15/06 | (2006.01) |
| G08G 5/00 | (2006.01) |
| G01N 21/17 | (2006.01) |
| G01N 15/00 | (2006.01) |

(52) U.S. Cl.
CPC .............. *H04N 7/183* (2013.01); *B64D 45/00* (2013.01); *G01N 15/06* (2013.01); *G01N 21/21* (2013.01); *G01N 21/41* (2013.01); *G01N 21/59* (2013.01); *G08G 5/0021* (2013.01); *G08G 5/0052* (2013.01); *G08G 5/0091* (2013.01); *G01N 2015/0046* (2013.01); *G01N 2015/0693* (2013.01); *G01N 2021/1793* (2013.01); *G01N 2021/4106* (2013.01); *G01N 2201/0214* (2013.01)

(58) Field of Classification Search
CPC .. G01J 5/60; G01J 5/0014; G01J 2005/0077; G08B 21/14; H04N 5/247; H04N 5/332; B64D 45/00; B64D 47/08; G01N 15/0205
See application file for complete search history.

(56) References Cited

U.S. PATENT DOCUMENTS

| | | | | |
|---|---|---|---|---|
| 4,363,967 A | * | 12/1982 | Efkeman ............... | G01J 5/0014 250/338.5 |
| 5,343,287 A | * | 8/1994 | Wilkins .................. | G01S 3/784 250/201.9 |
| 5,602,543 A | * | 2/1997 | Prata ........................ | G01J 5/60 250/338.5 |
| 5,654,700 A | * | 8/1997 | Prata ........................ | G01J 5/60 250/339.14 |
| 7,299,013 B2 | | 11/2007 | Rotta et al. | |

(Continued)

OTHER PUBLICATIONS

U.S. Appl. No. 12/949,873, "Volcanic Ash Detection by Optical Backscatter Using Standard Aircraft Lights," filed Nov. 19, 2010.

*Primary Examiner* — Neil Mikeska
(74) *Attorney, Agent, or Firm* — Ostrager Chong Flaherty & Broitman P.C.

(57) ABSTRACT

A system for detecting volcanic plumes using a camera on an aircraft, a distant point-like source of light, and a computerized method of processing images acquired by the camera to detect phenomena indicative of the presence of volcanic plumes in a volume of space intersected by light from the light source. A computer system is programmed to determine whether the image data from the camera has characteristics indicating that the imaged light had passed through a volcanic plume or not. In response to detection of a volcanic plume in the flight path of an aircraft, the computer system outputs an alert activation signal to an alert device that produces a visible or audible alert.

17 Claims, 7 Drawing Sheets (56) References Cited

U.S. PATENT DOCUMENTS

| | | | |
|---|---|---|---|
| 7,365,674 B2 | 4/2008 | Tillotson | |
| 7,592,955 B2 | 9/2009 | Tillotson | |
| 7,598,901 B2 | 10/2009 | Tillotson | |
| 7,623,065 B2 | 11/2009 | Tillotson | |
| 7,667,635 B2 | 2/2010 | Tillotson | |
| 7,728,759 B2 | 6/2010 | Tillotson | |
| 7,739,048 B2 | 6/2010 | Tillotson | |
| 7,872,603 B2 | 1/2011 | Tillotson | |
| 7,880,666 B2 | 2/2011 | Tillotson | |
| 7,889,122 B2 | 2/2011 | Tillotson | |
| 7,889,328 B2 | 2/2011 | Tillotson | |
| 8,174,431 B2 | 5/2012 | Tillotson | |
| 8,339,583 B2 | 12/2012 | Tillotson | |
| 8,345,115 B2 | 1/2013 | Tillotson | |
| 8,461,531 B2 | 6/2013 | Tillotson | |
| 8,471,730 B2 | 6/2013 | Tillotson | |
| 8,547,225 B2 | 10/2013 | Tillotson | |
| 8,666,570 B1* | 3/2014 | Tillotson | G06K 9/0063 340/945 |
| 8,917,385 B1* | 12/2014 | Lietzke | G01J 3/28 356/45 |
| 9,068,884 B1* | 6/2015 | Tillotson | G01J 1/38 |
| 2005/0151961 A1* | 7/2005 | McGraw | G01J 1/02 356/121 |
| 2009/0143988 A1* | 6/2009 | Tillotson | G01P 5/26 702/3 |
| 2009/0290025 A1* | 11/2009 | Cetin | G06K 9/6288 348/164 |
| 2011/0013016 A1* | 1/2011 | Tillotson | G01N 21/41 348/135 |
| 2012/0068862 A1* | 3/2012 | Tillotson | B64D 45/00 340/963 |
| 2012/0068863 A1* | 3/2012 | Tillotson | G01S 13/003 340/963 |
| 2012/0191350 A1* | 7/2012 | Prata | G01S 3/781 702/3 |
| 2012/0213436 A1* | 8/2012 | Grindstaff | G06T 5/008 382/167 |
| 2012/0274937 A1* | 11/2012 | Hays | G01S 17/58 356/337 |
| 2013/0087708 A1* | 4/2013 | Tillotson | G01N 21/71 250/338.5 |
| 2013/0135470 A1* | 5/2013 | Prata | G01S 3/781 348/144 |
| 2013/0226452 A1* | 8/2013 | Watts | G08G 5/0091 701/528 |
| 2014/0331161 A1* | 11/2014 | Venkataswamy | G06F 3/0484 715/771 |
| 2015/0019185 A1* | 1/2015 | Cunningham | G06F 17/5009 703/6 |
| 2015/0106059 A1* | 4/2015 | Ekanayake | G01M 15/14 702/182 |
| 2015/0316415 A1* | 11/2015 | Islam | G01J 3/453 250/338.4 |

* cited by examiner

VISUAL DETECTION OF VOLCANIC PLUMES

BACKGROUND

This invention generally relates to systems and methods for sensing when an aircraft is approaching a volcanic plume. As used herein, the term "volcanic plume" encompasses a cloud of volcanic ash suspended in a mass of gas that may include volcanic gases.

Volcanic plumes present two problems for aircraft: (a) engine shutdown due to ash; and (b) aircraft damage and/or crew and passenger injury due to ash and corrosive gases. Volcanic ash comprises tiny jagged particles of rock and natural glass blasted into the air by a volcano. Wind can carry ash thousands of miles, affecting far greater areas than other volcano hazards. Volcanic ash particles are extremely abrasive. They are jagged particles of rock and glass that can cause rapid wear to the internal workings of jet engines. More important, high temperatures in some parts of jet engines can melt the ash; it then re-solidifies on cooler parts of the engine, forming a layer that blocks airflow, interferes with moving parts, and eventually shuts down the engine.

Another issue is the potentially harmful effects of elevated concentrations of $SO_2$ and sulfate aerosol in ash-poor clouds on aircraft and avionics. In addition, volcanic ash particles, with sulfuric acid adhered thereto, are tiny enough to travel deep into the lungs of human beings, which may be harmful and potentially fatal to people.

Pilots are advised to avoid visible volcanic plumes. This is not always possible. Diffuse volcanic ash is hard to distinguish from smoke or thin cirrus. On moonless nights, volcanic ash may be invisible. Airborne weather radar is no help because ash particles have virtually no radar signature. Onboard laser scattering instruments work reasonably well at detecting volcanic ash, but such instruments are heavy, increase drag, and give no advance warning before the airplane is actually flying through a volcanic plume.

The overall technical problem is to provide means for detecting airborne volcanic ash at cruise altitude and then alerting aircraft so they can avoid damage or injury from passage through the volcanic plume. General approaches to solving the specific technical problem of detecting the presence of volcanic ash particles in the atmosphere surrounding an aircraft include at least the following:

1. See and Avoid. In daytime clear weather, pilots can see and avoid the visually distinctive cloud from an erupting volcano.

2. Geological Reports. For volcanoes that are well monitored, sensors or people on the ground can quickly observe an eruption and report it to flight safety authorities such as the FAA. In these cases, a notice to airmen is issued.

3. Satellite Observations. A few satellites are capable of detecting volcanic plumes from orbit, based on the sulfur dioxide spectra, the thermal infrared emission, visible volcanic plumes, or a combination of these. When a satellite detects a volcanic plume, a notice to airmen is issued.

4. Plume Forecasts. Given geological reports or satellite observations, the national weather services of various countries predict where the volcanic plume will go at various times. Operators use these forecasts to choose safe routes.

5. Radio-Frequency Occultation. Volcanic emissions of hydrogen sulfide have refractive effects on radio signals from satellites. The effects can be detected and used to warn aircraft of volcanic The drawbacks of the foregoing approaches are as follows:

1. See and Avoid. Volcanic plumes are often encountered during nighttime and/or embedded within other clouds. Therefore, visual detection is not always effective.

2. Geological Reports. Many remote volcanoes around the world are still not well instrumented and can erupt without immediate detection. Even after detection, the mechanism to issue a notice to airmen imposes a delay for processing and distribution, during which an unwarned aircraft may encounter the plume.

3. Satellite observations are not continuous. An eruption that occurs between satellite passes may go undetected for 6 to 12 hours, which is more than enough time for aircraft to encounter the plume. The period of non-detection may go on longer for small eruptions or during overcast conditions. Even after detection, the mechanism to issue a notice to airmen imposes a delay for processing and distribution, during which an unwarned aircraft may encounter the plume.

4. Plume forecasts have large margins of error, so regulators impose large keep-out zones around the most likely plume location, especially at night. Aircraft may fly 100 miles farther out of their way than necessary because of uncertainties in the forecasts. This costs passengers time and costs operators money.

5. Radio-frequency (RF) occultation requires specialized RF receivers. Not all aircraft operators may be able to afford them. Further, it does not detect thin clouds of volcanic ash: essentially all volcanic gases dissipate from the ash after a few days.

It would be desirable to provide means for remotely visually detecting airborne volcanic ash at cruise altitudes without the above-described drawbacks.

SUMMARY

The subject matter disclosed herein comprises a system for detecting volcanic plumes using a camera, a distant point-like source of light, and a computerized method of processing images acquired by the camera in a manner that detects image features indicative of the presence of volcanic plumes in a volume of space intersected by the light received by the camera from the light source. Although the techniques disclosed herein are primarily aimed at detecting volcanic plumes at night when many distant point-like light sources are visible, these techniques are also useful under some daylight conditions.

The system comprises a camera, a computer system programmed to process the image data acquired by the camera, and an alert device which is activated when the computer system detects image data representing visual features indicative of a volcanic plume-induced effect. Although the embodiments disclosed in detail below involve the installation of a camera onboard an airplane, in alternative embodiments the camera platform could be a rotorcraft, a missile, a balloon (including a weather balloon), a spacecraft, or other air vehicle; the camera could even be on a terrestrial platform. The camera may work entirely within the human visual spectrum, or may extend into the infrared or ultraviolet.

In addition, although the embodiments disclosed in detail below involve an alert device installed on the same airplane that carries the camera, the alert device may instead be at some remote location connected to the camera by a radio network. For example, the alert device may be located in an air traffic management center or in an airline dispatch office.

Furthermore, the term "distant point-like light sources" as used herein refers to a class of objects that includes more than stars. The sun or moon could be used as a light source with only slight modification to most of the methods described below (i.e., excluding scintillation-based methods). In all cases, the distant point-like light source must be positioned behind the volume in which a volcanic plume may be present. There are about 3600 stars visible to the naked eye. A long exposure by a digital camera can see even more stars. Alternative embodiments may use bright planets or artificial satellites. Other alternative embodiments may use lights on the ground, such as airport beacons, to reveal volcanic plumes at altitudes lower than the camera. Distant airplanes can also serve as point-like light sources. The camera can capture images of the landing lights or strobe lights of distant airplanes, or sunlight reflected from the skin of a distant airplane (though the latter technique does not work for measuring scintillation—the angular extent of an airplane is too large for amplitude scintillation).

Some embodiments may rely not only on direct measurements with a camera, but may also use information from off-board sources (e.g., weather forecasts, volcanic plume forecasts, or volcanic plume by starlight databases of intensity versus wavelength for various stars) to improve measurements, selection of light sources, or probability estimates.

In accordance with the embodiments disclosed in detail hereinafter, the system comprises the following: an aircraft; a camera on the aircraft, having known orientation with respect to the aircraft; a computer system programmed to detect image features indicative of a volcanic plume; and a display or warning device. The process for detecting volcanic plumes comprises the following operations: (a) installing a camera on an aircraft; (b) flying the aircraft to a location from which a star-like light source may be visible and a volcanic plume may exist between the aircraft and the light source; (c) using the camera to capture at least one image of the light source; (d) transferring the image data to a computer system; (e) performing calculations to determine whether the image data acquired by the camera has characteristics that correspond to image features indicating that the light had propagated through a volcanic plume; and (f) if the image data has characteristics that correspond to image features indicative of a volcanic plume, issuing a warning or display information about the suspected volcanic plume. The computer system is programmed to identify characteristics in the image data that correspond to one or more volcanic plume-induced effects on light, such as changes in refraction, scintillation, dimming/occlusion, color shift, changes in polarization, and corona shape. The identification of some of these phenomena requires the camera to capture and the computer system to analyze multiple images in a sequence.

One aspect of the subject matter disclosed in detail herein is a system for detecting airborne volcanic ash comprising: a camera that outputs image data representing captured images; and a computer system in communication with the camera for receiving the image data, wherein the computer system is programmed to process the image data from the camera to determine whether at least some of the image data represents one or more visual features in the captured images which are indicative of a volcanic plume-induced effect on light or not. The system may further comprise an alert device in communication with the computer system, wherein the computer system is further programmed to send an alert activation signal to the alert device in response to a determination that some image data represents one or more visual features indicative of the volcanic plume-induced effect on light from a distant point-like light source. In one embodiment, the camera and computer system are carried by an air vehicle. The volcanic plume-induced effect comprises one or more of the following: change in refraction, scintillation, dimming, color shift, change in polarization, and corona shape.

Another aspect is a method to detect airborne volcanic ash, comprising: attaching a camera to an air vehicle; flying the air vehicle to a location from which volcanic ash may be visible; capturing image data for at least one image of a distant point-like light source using a camera; and analyzing the image data to detect at least one visual feature indicative of the presence of a volcanic plume in a space between the air vehicle and the distant point-like light source using a computer system. The method may further comprise: generating an alert activation signal in response to detecting at least one visual feature indicative of the presence of a volcanic plume in the space between the air vehicle and the distant point-like light source; and issuing a visible or audible alert in response to generation of the alert activation signal. Again, the visual features are selected from a group comprising: change in refraction, scintillation, dimming, color shift, change in polarization, and corona shape.

A further aspect of the subject matter disclosed herein is a system for detecting airborne volcanic ash comprising: an air vehicle; a camera carried by the air vehicle, the camera outputting image data representing captured images; a computer system disposed onboard the air vehicle and in communication with the camera for receiving the image data, wherein the computer system is programmed to process the image data from the camera to determine whether at least some of the image data represents one or more visual features in the captured images which are indicative of a volcanic plume-induced effect or not; and an alert device in communication with the computer system. The computer system is further programmed to send an alert activation signal to the alert device in response to a determination that some image data represents one or more visual features indicative of the volcanic plume-induced effect.

The system and methods described above have advantages over the known approaches. First, the methods disclosed herein use a star-like light source. Stars are most visible at night. Therefore the methods disclosed herein can be used to complement the see-and-avoid approach: the methods disclosed herein work best during moonless nights when the see-and-avoid approach works worst. Second, the methods disclosed herein detect volcanic plumes and issue warnings to aircraft in real time, so there is minimal delay. Since the system disclosed herein is onboard an aircraft, it can detect a volcanic plume that is encroaching on an airway even if the plumes come from unmonitored volcanoes. This allows regulators to impose smaller keep-out zones around the forecast plume location, knowing that aircraft equipped with the system disclosed herein can detect and avoid plumes if the forecasts are incorrect. Third, the methods disclosed herein use equipment which is much smaller and cheaper and has superior performance compared to the equipment used in RF occultation.

Other aspects are disclosed in the detailed description that follows.

BRIEF DESCRIPTION OF THE DRAWINGS

Reference will hereinafter be made to the drawings in which similar elements in different drawings bear the same reference numerals.

DETAILED DESCRIPTION

Figure 1:
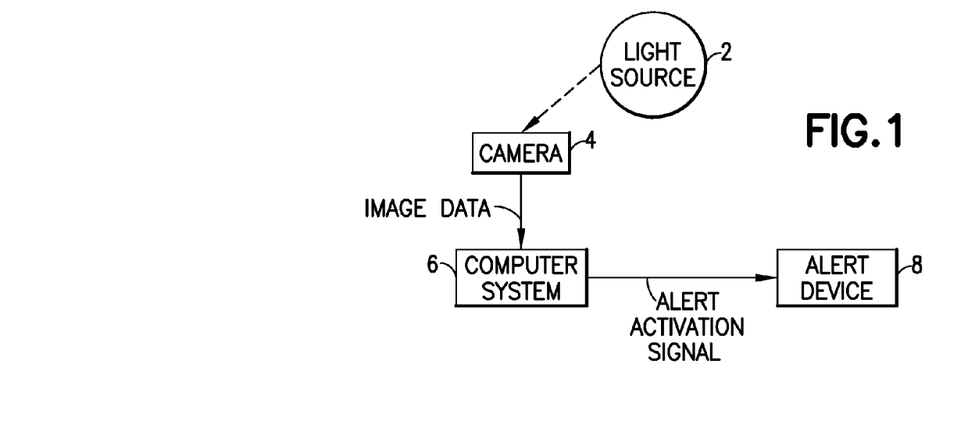
FIG. 1 is a block diagram showing components of a system for issuing an alert in response to detection of light from a distant point-like light source having characteristics indicative of the presence of a volcanic plume.

FIG. 1 is a block diagram showing some components of a system for issuing an alert in response to detection of light that has visual features indicative of propagation through a volcanic plume. Light (indicated by a dashed arrow) from a distant point-like light source 2 propagates through space and impinges on a camera 4. The camera 4 converts impinging light radiation into digital image data, which image data can be exported or transmitted to a computer system 6 using well-known wireline or wireless coupling means. The computer system 6 is programmed to detect image data representing visual features indicative of a volcanic plume-induced effect. In other words, the computer system 6 is programmed to determine whether the image data from the camera has characteristics indicating that the imaged light had passed through a volcanic plume or not. If the image data has characteristics indicating that the imaged light had passed through a volcanic plume, the computer system outputs an alert activation signal to an alert device 8. The alert device 8 may comprise, for example, a display screen that produces a visual alert or an annunciator that produces an audible alert. The visual alert may be a flashing brightly colored message; the audible alert may be a repetitive verbal warning.

In accordance with various embodiments, the computer system 6 may be programmed to identify characteristics in the image data that correspond to one or more volcanic plume-induced effects, such as changes in refraction, scintillation, dimming/occlusion, color shift, changes in polarization, and corona shape. The identification of some of these phenomena requires the camera 4 to capture and the computer system 6 to analyze multiple images in a sequence.

Various embodiments that employ detection of volcanic plumes using a camera which is installed on an airplane will now be described in detail for purposes of illustration only. In accordance with these embodiments, the camera is directed forward from an airplane and toward a star, but the camera could just as well be directed aft or to the side. An onboard computer system is programmed to process image data acquired by the camera in a manner that detects visual features indicating that captured starlight had propagated through a volcanic plume. However, the equipment disclosed herein could also be used to detect light from other types of point-like light sources, such as bright planets, artificial satellites, airport beacons, landing lights or strobe lights of a distant airplane, and so forth.

Various methodologies for detecting volcanic plumes will now be described in detail for purposes of illustration only. These methodologies detect changes in various properties of light which may be induced by passage through a volcanic plume. The phenomena discussed below include the following: changes in refraction, scintillation, dimming/occlusion, color shift, changes in polarization, and corona shape. Each of these phenomena has some utility in detecting nebulous visual obstructions and determining whether a given obstruction is a cloud of ice crystals, a plume of smoke, or a plume of volcanic ash. Alternative embodiments may be configured to measure features or characteristics of any one or any combination of these phenomena. In addition, some embodiments may use data fusion methods known in the art to combine evidence from multiple phenomena into a more reliable estimate of the likelihood that volcanic ash is present.

Change in Refraction

A volcanic plume may refract, or bend, the path of light from the point-like light source to the camera. The changes in refraction arise from two factors.

One factor is the composition of the gases in the volcanic plume. A young plume may contain common volcanic gases like hydrogen sulfide, carbon dioxide, or others. These gases have a higher refractive index than air. Therefore, light slows as it passes through a plume containing these gases; its path bends toward the higher concentration of these gases. This does not occur for plumes more than a few days old: by then, the volcanic gases have diffused away from the ash or have chemically reacted with moisture and become other chemicals.

Figure 2:
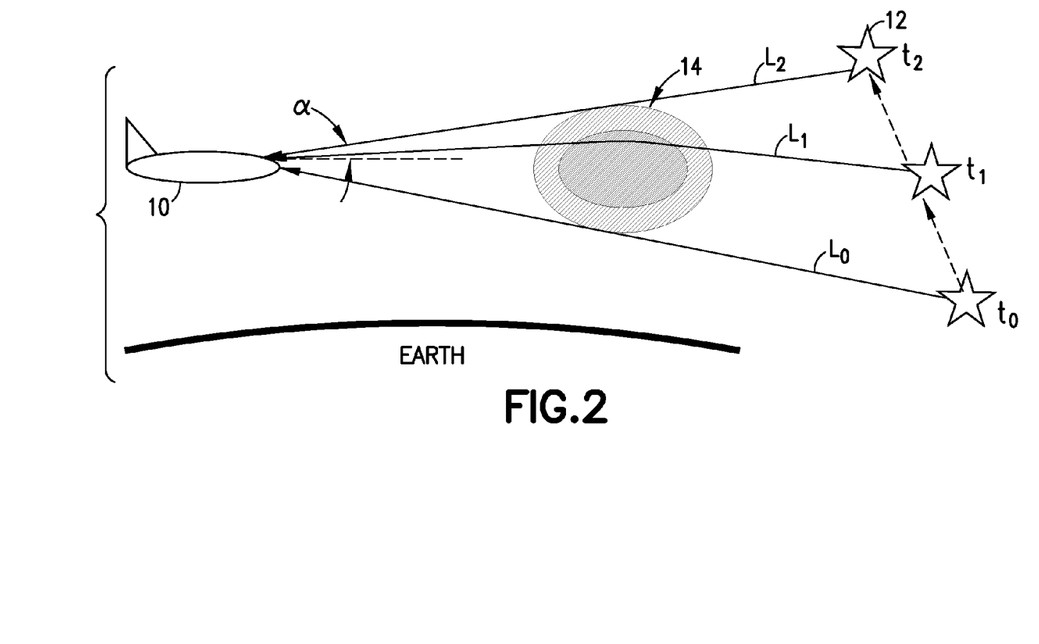
FIG. 2 is a diagram showing an airplane receiving light from a star at three instances in time in a scenario wherein a cold volcanic plume (indicated by shading) disposed between the star and the airplane refracts light from the star before it reaches the airplane.

FIG. 2 depicts a situation wherein a volcanic plume 14 (indicated by shading) including volcanic gases is disposed between an airplane 10 and a star 12. The airplane 10 has an onboard camera (not shown) installed in its nose. FIG. 2 shows three paths $L_0$, $L_1$ and $L_2$ of light from star 12 that is captured by the camera at respective times $t_0$, $t_1$ and $t_2$. (For the purpose of simplification, the changing locations of the aircraft 10, which is moving, are not shown.) Light paths $L_0$ and $L_2$ do not pass through the volcanic plume 14, but light path $L_1$ does. The volcanic plume 14 causes the light propagating along light path $L_1$ to refract toward the cool region.

The other factor affecting refraction is temperature. Cool air is denser and has a higher refractive index, so light passing through a plume of cool air bends toward the cool region in the manner depicted in FIG. 2. Warm air is less dense and has a lower refractive index, so light passing through a plume of warm air bends away from the warm region. A plume of volcanic ash often has a different temperature than the surrounding air because ash is better than air at absorbing sunlight and emitting infrared radiation. As a general rule, a volcanic plume makes air warmer in daylight and cooler at night, but specific weather conditions can change this.

Figure 3:
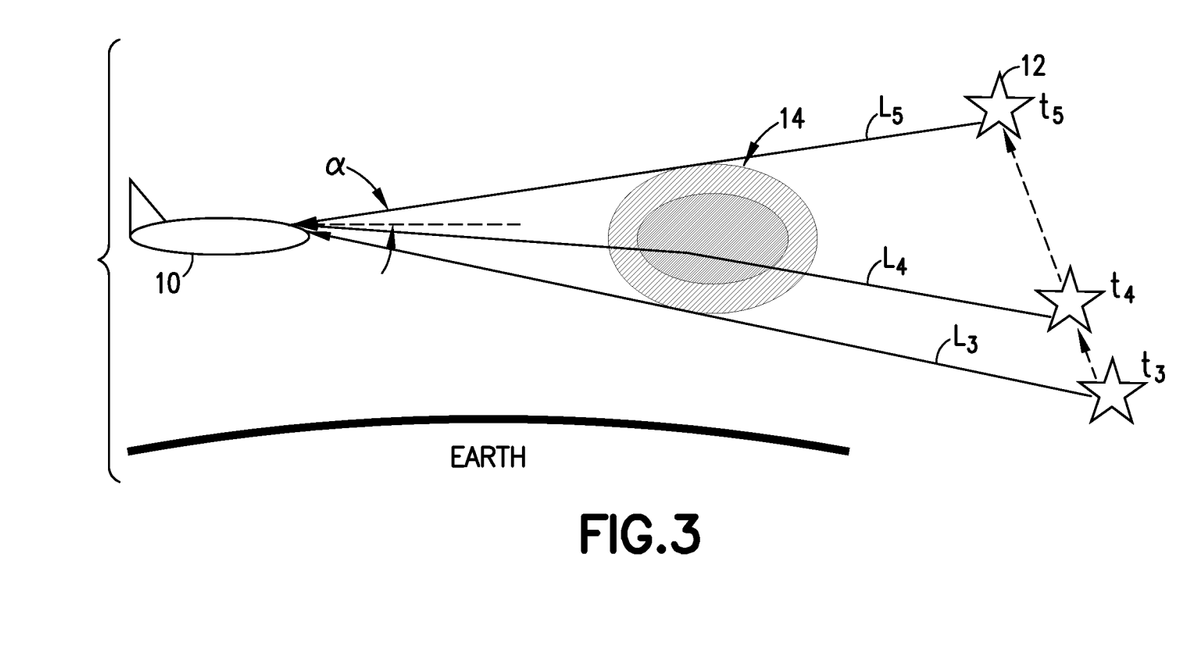
FIG. 3 is a diagram showing an airplane receiving light from a star at three instances in time in a scenario wherein a hot volcanic plume (indicated by shading) disposed between the star and the airplane refracts light from the star before it reaches the airplane.

FIG. 3 depicts a situation wherein a warm volcanic plume 14 (indicated by shading) is disposed between an airplane 10 and a star 12. The airplane 10 has an onboard camera (not shown) installed in its nose. FIG. 3 shows three paths $L_3$, $L_4$ and $L_5$ of light from star 12 that is captured by the camera at respective times $t_3$, $t_4$ and $t_5$. (Again, the changing locations of the aircraft 10 are not shown.) Light paths $L_3$ and $L_5$ do not pass through the volcanic plume 14, but light path $L_4$ does. The warm volcanic plume 14 causes the light propagating along light path $L_1$ to refract away from the warm region.

In accordance with one embodiment of the system partially depicted in FIG. 1, the computer system 6 is programmed to calculate the apparent position of the light source 2 based on the location (i.e., position and orientation) of the camera and the image data captured by the camera 4 and then compare that calculated position to the light source's known position. For a star, planet, or artificial satellite, the position is available from an ephemeris. For a distant aircraft, the position is available by radio if the aircraft has a digital navigation system and is connected to a communications network through which to report its position. When the known position (adjusted for the refraction caused by the atmosphere's normal density gradient) differs from the apparent position by more than some user-selected threshold, the computer system 6 generates an alert activation signal and the alert device 8 then issues a visible or audible alert signal warning the pilot that the airplane may be approaching a volcanic plume. In some embodiments, the system measures only the elevation angle, a, above the local horizontal, indicated by a dashed line in FIG. 2. In other embodiments, the system measures both elevation and azimuth angles.

A single refraction measurement is not enough to verify and locate a volcanic plume with much precision. In a more sophisticated embodiment, the camera 4 captures a series of images. As the aircraft moves, its position changes relative to the light source, e.g., for a star ahead of the aircraft, the light source appears to rise higher above the horizontal, as seen in FIG. 2 (from time $L_0$ to time $L_2$) and FIG. 3 (from time $L_3$ to time $L_5$). The path of light from star 12 to airplane 10 passes through different parts of the volcanic plume 14 at different times, so the direction and magnitude of refraction changes. The computer system measures this refractive change over time and uses it to better estimate the location, extent, and refractive index of a possible volcanic plume.

Unusual refraction by itself is evidence of a volcanic plume, but is not a perfectly reliable indicator. Smoke has similar thermal behavior: it absorbs sunlight and emits infrared radiation. The detection of other phenomena (described below) can help distinguish smoke from volcanic ash.

Scintillation

Because a volcanic plume is often warmer or cooler than surrounding air, parts of the plume may rise or fall, creating turbulence. Referring again to FIG. 1, this turbulence will cause the light captured by the camera 4 to flicker or scintillate, i.e., the distant point-like light source 2 appears brighter and dimmer over a series of images. This flickering typically has temporal frequencies higher than 10 Hz. The magnitude of flickering displays a log-normal probability distribution. These characteristics distinguish turbulence-induced scintillation from the intermittent dimming and occlusion caused by clouds or plumes. The computer system 6 can be programmed to distinguish image data produced during turbulence-induced scintillation from image data produced during intermittent dimming and occlusion caused by clouds or plumes In mature plumes, scintillation has the same root cause as refraction, namely, heat. Accordingly, the computer system 6 can be programmed to process respective image data sets representing the effects of scintillation and refraction. These phenomena can produce sets of image data which serve as mutually reinforcing evidence for the presence of a volcanic plume in a region located between the airplane and the point-like light source. When both refraction and scintillation are detected, the computer system can be programmed to deduce that there is a high likelihood that a volcanic plume has induced these phenomena and then generate an alert activation signal. The computer system can be programmed to determine that when both refraction and scintillation are detected, the presence of a volcanic plume is more probable than the sum of their individual evidentiary weights.

In accordance with one specific implementation, the computer system 6 can be programmed to generate an alert activation signal in response to obtaining any of the following calculation results: (1) a first parameter, that is a function of the amount of refraction, exceeds a first threshold while a second parameter, that is a function of the amount of scintillation, does not exceed a second threshold; (2) the first parameter does not exceed the first threshold but the second parameter exceeds the second threshold; and (3) the first parameter exceeds a third threshold that is less than the first threshold and the second parameter exceeds a fourth threshold that is less than the second threshold.

In accordance with another specific implementation, the computer system 6 can be programmed to generate an alert activation signal in response to obtaining any of the following calculation results: (1) a first parameter, that is a function of the amount of refraction, exceeds a first threshold while a second parameter, that is a function of the amount of scintillation, does not exceed a second threshold; (2) the first parameter does not exceed the first threshold but the second parameter exceeds the second threshold; and (3) the first parameter is less than the first threshold while the second parameter is less than the second threshold, but the sum of first and second products exceeds a third threshold, the first product being equal to the first parameter times a first weighting factor and the second product being equal to the second parameter times a second weighting factor.

Alternative volcanic plume detection algorithms based on refraction and scintillation can be readily implemented by persons skilled in the art.

Turbulence and scintillation sometimes occur in the absence of a volcanic plume. Therefore, for scintillation to be a strong indicator of the presence of a volume plume, the scintillation should occur with other plume-induced phenomena of the types described herein.

Dimming and Occlusion

Volcanic plumes scatter or absorb some light from the light source. As a result, the light source appears dimmer to the camera. In a mature volcanic plume, the ash has had time to spread out. Edges of a mature volcanic plume are diffuse and tenuous; changes in ash density within the plume are gradual. Therefore, dimming observed by the camera increases gradually as the airplane moves to position the light source behind the plume. Fluctuations as the light source crosses behind the volcanic plume are likewise gradual, even if they eventually produce a deep fade in intensity.

Figure 4A:
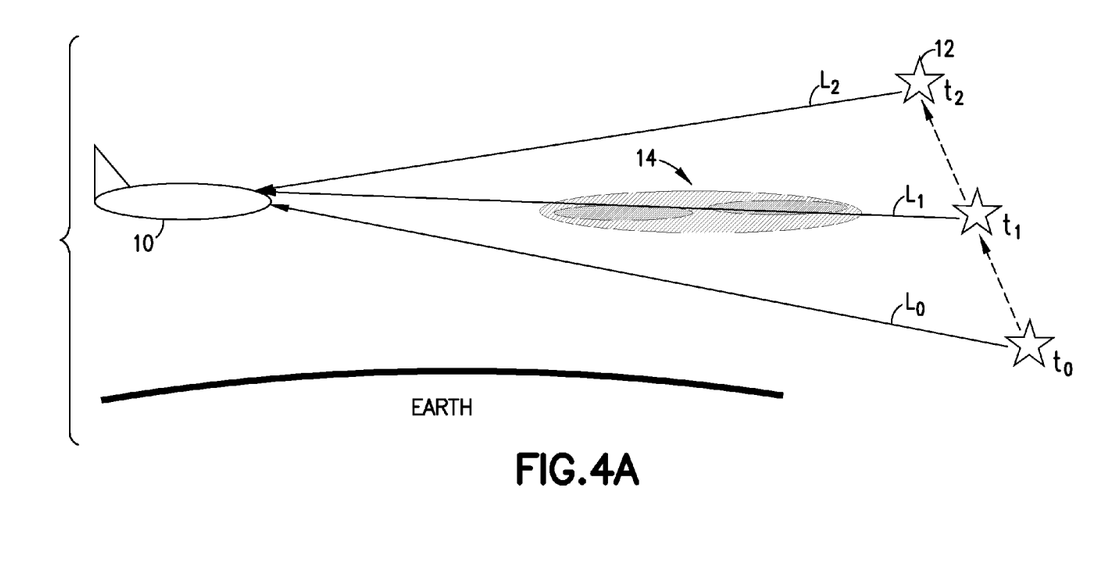
FIG. 4A is a diagram showing an airplane receiving light from a star at three instances in time in a scenario wherein a volcanic plume (indicated by shading) disposed between the star and the airplane scatters and/or absorbs light from the star before it reaches the airplane, producing gradual occlusions.
Figure 4B:
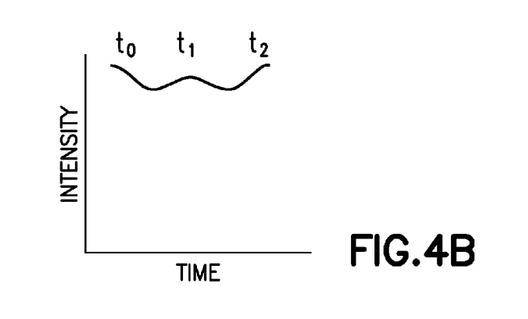
FIG. 4B is a graph showing gradual changes in the intensity of starlight received by the camera onboard the airplane in the scenario depicted in FIG. 4A.

FIG. 4A shows an airplane 10 receiving light from a star 12 at three instances in time in a scenario wherein a volcanic plume 14 (indicated by shading) disposed between the star 12 and the airplane 10 scatters and/or absorbs light from the star 12 before it reaches the airplane 10, thereby producing gradual occlusions in images captured by a camera onboard the airplane 10. FIG. 4B is a graph showing gradual changes in the intensity of starlight received by the camera onboard the airplane 10 in the scenario depicted in FIG. 4A.

Meteorological clouds also scatter and absorb light. However, the physics of condensation, sublimation, and evaporation dictate that meteorological clouds have a tighter spatial distribution than clouds of stable materials like ash and smoke. Water droplets and ice crystals exist within a sharply bounded set of conditions and vanish when they leave those conditions. Even in cirrus clouds, the spatial density of ice crystals varies strongly over relatively small distances. As a result, dimming caused by a meteorological cloud increases and decreases more sharply than for a mature volcanic plume. The change is not just one of magnitude, but of relative frequency distribution: dimming by a meteorological cloud has relatively stronger high-frequency spatial components for a given amount of dimming.

Figures 5A, 5B:
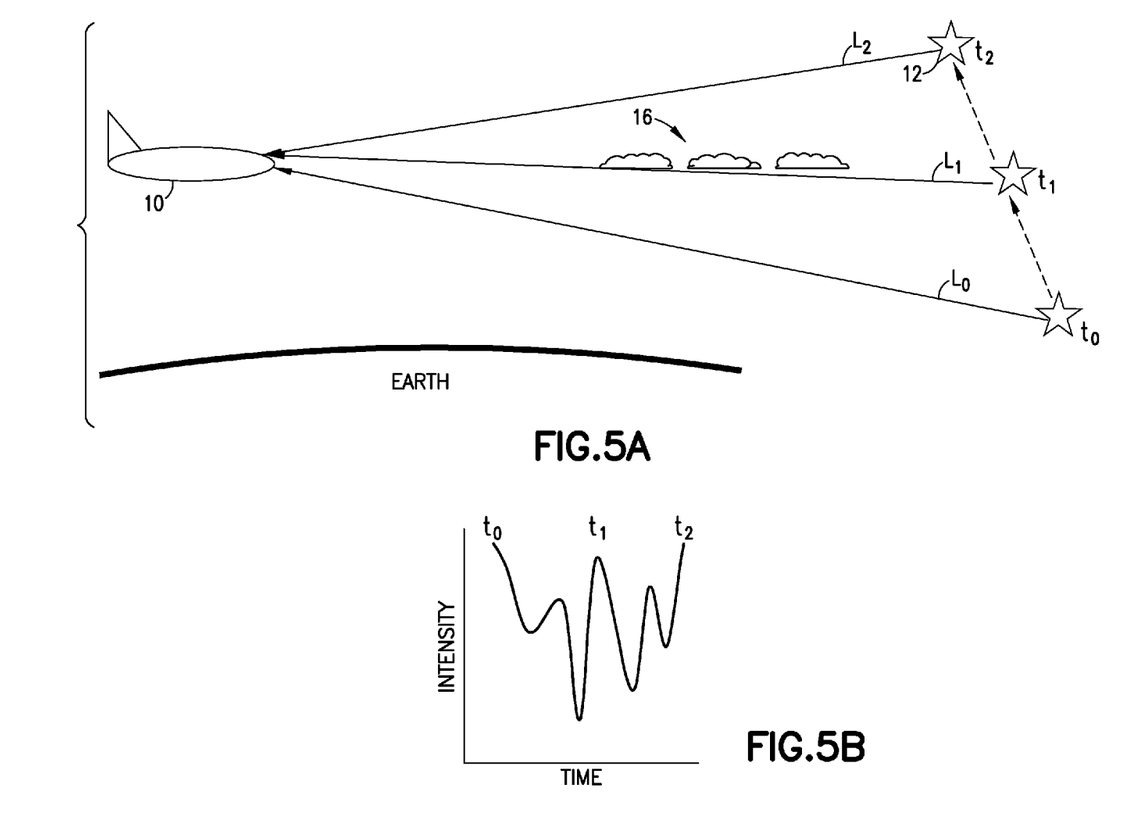
FIG. 5A is a diagram showing an airplane receiving light from a star at three instances in time in a scenario wherein meteorological clouds disposed between the star and the airplane scatter and/or absorb light from the star before it reaches the airplane, producing sharp, strong occlusions.
FIG. 5B is a graph showing sharp, strong changes in the intensity of starlight received by a camera onboard the airplane in the scenario depicted in FIG. 5A.

FIG. 5A shows an airplane 10 receiving light from a star 12 at three instances in time in a scenario wherein meteorological clouds disposed between the star 12 and the airplane 10 scatter and/or absorb light from the star 12 before it reaches the airplane 10, thereby producing sharp, strong occlusions in images captured by a camera onboard the airplane 10. FIG. 5B is a graph showing sharp, strong changes in the intensity of starlight received by a camera onboard the airplane 10 in the scenario depicted in FIG. 5A.

In accordance with further embodiments of the system partially depicted in FIG. 1, the computer system 6 can be further programmed to use dimming of the light source 2 to detect a possible volcanic plume. The computer system 6 analyzes the putative plume's spatial characteristics (indicated by the dimming pattern versus time, i.e., $I(t)/I_0$, where $I(t)$ is each sample measurement of the light source's intensity at time t and $I_0$ is the undimmed intensity measured before an encounter with a possible plume) to discriminate a volcanic plume or a smoke plume from meteorological clouds. This analysis of the dimming versus time may include:

1. Computing the optical depth, $\tau=-\ln(I(t)/I_0)$, for each sample; computing the fractional deviation, $S=\sigma(\tau)/\text{mean}(\tau)$, over all samples in a given spatial or temporal window, e.g., a spatial window of 1 kilometer of motion perpendicular to the line of sight or a temporal window of 10 seconds, where $\sigma(\tau)$ is the standard deviation of $\tau$ and mean $(\tau)$ is the average; comparing S to a user-selected threshold; and, if S exceeds the threshold while mean optical depth exceeds a second user-selected threshold, issuing a warning.

2. Computing the optical depth as above for each sample; computing the Hurst exponent, H, for the set of samples in a given spatial or temporal window; computing the sample's fractal dimension D by the well-known relation D=2-H; comparing D to a user-selected threshold; and, if D is below the threshold while mean optical depth exceeds a second user-selected threshold, issuing a warning.

3. Computing the spatial Fourier transform $F(k)$ or the temporal Fourier transform $F(\omega)$ of samples in a given spatial or temporal window where k is the spatial wave number and $\omega$ is the temporal angular frequency; computing the slope a of $F(k)$ or $F(\omega)$; comparing the slope a to a user-selected threshold; and, if a is below the threshold while mean optical depth exceeds a second user-selected threshold, issuing a warning. (This works because clouds have relatively stronger high-frequency spatial components than volcanic plumes. For volcanic plumes, slope a is strongly negative, i.e., the high-frequency components are much weaker than the low-frequency components. For clouds, slope a is negative, but less negative than for ash: the high-frequency components fall off more slowly with frequency.)

The foregoing analyses can be utilized in conjunction with other programs (previously described) that use refraction and/or scintillation to compute a probability that a volcanic plume is present in the space between an airplane and a distant point-like light source.

Color Shift

Figure 6:
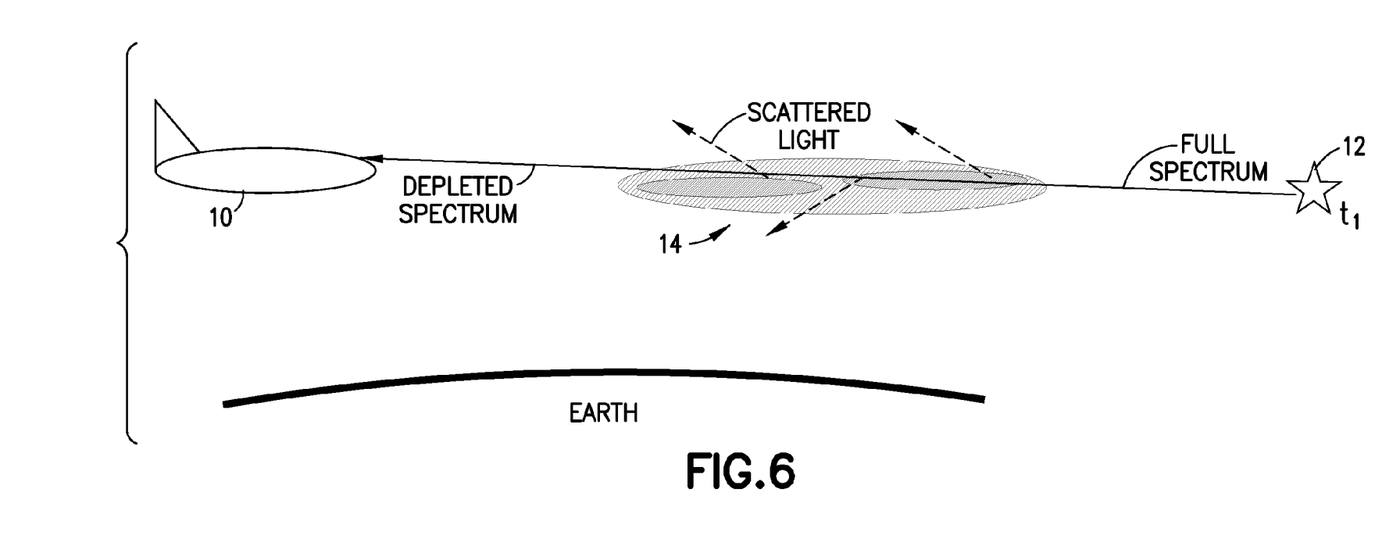
FIG. 6 is a diagram showing an airplane receiving light from a star in a scenario wherein a volcanic plume disposed between the star and the airplane scatters light from the star before it reaches the airplane, producing changes in the spectrum of transmitted light.

Volcanic plumes scatter some light from the light source, so only a fraction of the originally transmitted light reaches the camera onboard the airplane. FIG. 6 shows an airplane 10 receiving light from a star 12 in a scenario wherein a volcanic plume 14 disposed between airplane 10 and star 12 scatters light (indicated by dashed arrows) from star 12 before it reaches the airplane 10, producing changes in color in the images captured by the onboard camera (not shown in FIG. 6). The size of the scattering particles affects which wavelengths of light are most strongly scattered. In a mature volcanic plume, large particles of ash have had time to settle out; typical remaining particles are smaller than 30 microns (0.0012 inch) in diameter. In addition, a typical ash particle has many features (see FIG. 8)—glass spherules, fragments of stone bubbles, and jagged edges or corners—that are only one or two microns in size. This is only slightly larger than the wavelength of red light. As a result, ash particles usually exhibit strong Mie scattering of red wavelengths. Blue light is less strongly scattered. The depleted spectrum of light reaching the camera (see FIG. 6) is usually bluer than full spectrum of light from the light source.

In contrast, most high-altitude clouds and smoke strongly attenuate blue light via Rayleigh scattering. The depleted spectrum reaching the camera is redder than light from the light source.

In accordance with an alternative embodiment of the system shown in FIG. 1, camera 4 has the capability to capture color images, while computer system 6 is programmed to process the image data to determine whether the image data indicates dimming accompanied by a shift to bluer wavelengths. A positive correlation of dimming with blue color is evidence that volcanic ash is present in the space between the camera and a distant point-like light source. Conversely, dimming accompanied by a shift to redder wavelengths is evidence that nonvolcanic clouds or smoke are present.

The general rule of volcanic ash scattering red light and other particles scattering blue light has some exceptions, so a more sophisticated embodiment uses information about current conditions in the area. For example, if a volcanic eruption is underway and geologists or meteorologists have forecast the typical size of ash particles in the area, the computer system 6 may be programmed to use that information to estimate how much color change in which direction (red or blue) corresponds to how much ash-induced dimming. Likewise, if there is a smoke cloud and the weather service has determined by measurement a typical size range for smoke particles in the cloud or has measured scattering characteristics of the cloud, the computer system 6 may be programmed to use that information to improve its ability to recognize that type of smoke.

Change in Polarization

Figure 7A:
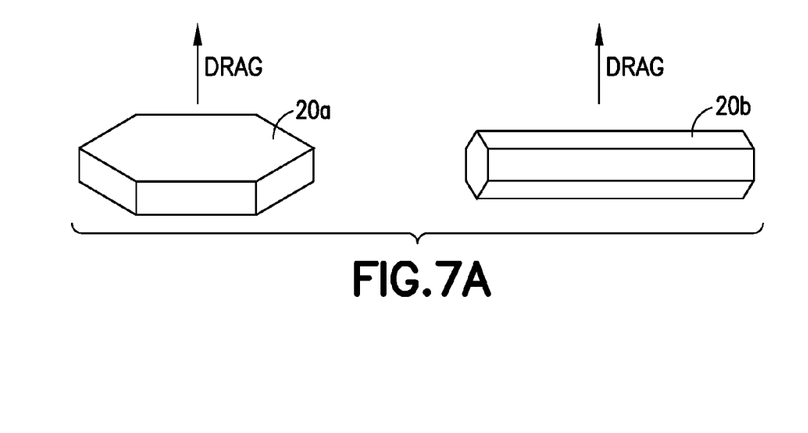
FIG. 7A is a diagram showing flat and horizontal ice crystal shapes.
Figure 7B:
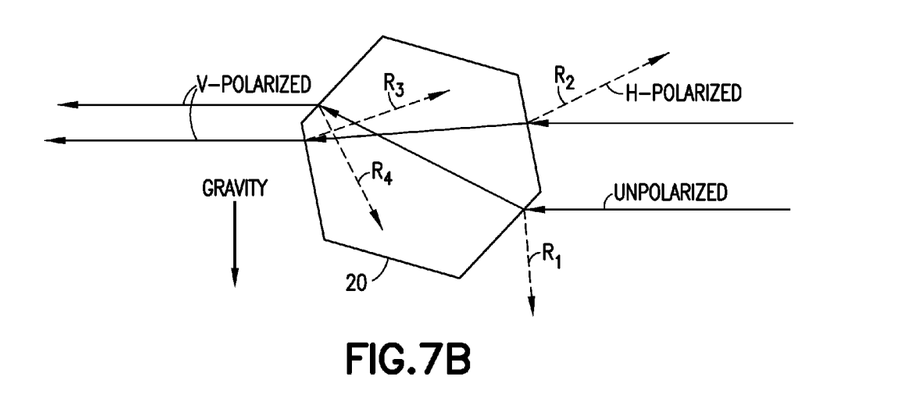
FIG. 7B is a diagram showing paths of polarized light resulting from light impinging upon an ice crystal.

Besides changing the intensity and color of light, passage through a plume or cloud can also change light's polarization. Ice crystals are an extreme example. Ice crystals are polyhedra, i.e., convex objects with flat faces. They also have fairly large aspect ratios. Aerodynamic forces (e.g., drag) tend to orient such objects 20a and 20b with their long axes perpendicular to their motion through the air, as depicted in FIG. 7A. Therefore, ice crystals in stable air orient themselves horizontally. As shown in FIG. 7B, when light passes through a cirrus cloud, the light often passes through an ice crystal 20, emerging with the same direction as it entered. Because the ice crystal 20 is disposed horizontal relative to the incoming light, the partial reflections $R_1$, $R_2$, $R_3$, and $R_4$ at respective surfaces have more horizontally polarized light than vertically polarized. Light that reaches the camera therefore has more vertical polarization.

Different types of clouds and plumes have particles with different shapes. Ice crystals, as described above, are usually flat and horizontally oriented. Light scattered from an ice cloud has the strongest horizontal polarization, so light traversing an ice cloud has the strongest vertical polarization for a given amount of dimming.

Figure 8:
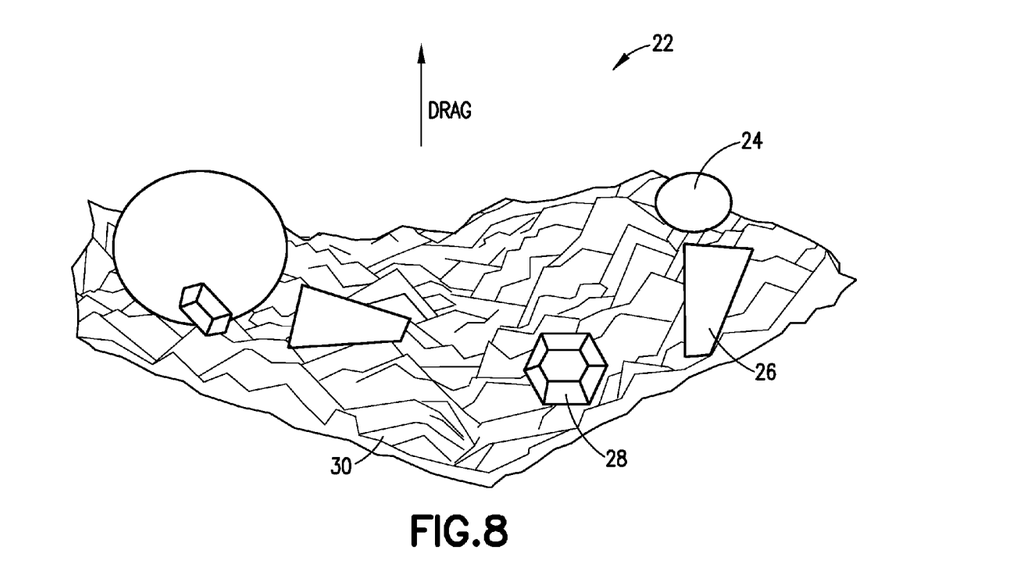
FIG. 8 is a diagram depicting (simplistically) a typical ash particle comprising a fragment of tephra with glass and feldspar accretions.

FIG. 8 depicts a typical ash particle 22 comprising a primary tephra body 30 with accretions such as glass spherule 24, shard 26 and mineral crystal 28. Volcanic ash particles also tend to have a large aspect ratio, so aerodynamic forces (such as drag, indicated by an arrow in FIG. 8) give them a horizontal orientation. However, ash particles are rough and highly irregular. A large minority of ash surfaces from which light scatters are vertical or intermediate rather than horizontal. Therefore, light scattered from volcanic ash has only moderate horizontal polarization, and light traversing a volcanic plume has moderate vertical polarization for a given amount of dimming.

Smoke particles have highly irregular surfaces, but their overall shape tends to be nearly spherical (not shown), especially for the fine-grained smoke that remains at airliner cruise altitudes for days or weeks. Light passing through smoke incurs very little polarization.

In accordance with some embodiments, a polarizing filter can be placed in front of the camera 4 (see FIG. 1) or other ways to measure polarization of light from the light source can be provided. In these embodiments, the computer system 6 can be programmed to calculate a ratio of the degree of polarization to the amount of dimming. When the ratio of the degree of vertical polarization to the amount of dimming falls within a range corresponding to moderate (but not strong) vertical polarization, the computer system 6 sends an alert activation signal to the alert device 8, which then issues a visible or audible warning indicating the presence of volcanic ash along the intended flight path.

Corona Shape

The scattering that produces polarization also produces an effect called corona, which is a set of one or more prismatically colored rings of light that surrounds a distant light source. (Typical corona rings are depicted by shading in FIGS. 9A through 9C.) For example, when one views the moon through a thin cloud, the moon appears to be surrounded by a ring of light that fades to invisibility one or two angular degrees away from the moon (measured from the vantage point of an observer on Earth). The shape and orientation of particles in a cloud or plume affect the direction in which light is scattered.

Figure 9A:
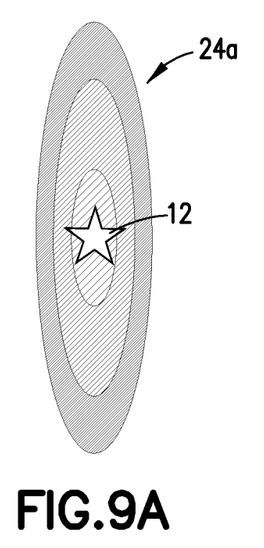
FIGS. 9A through 9C are diagrams depicting different model corona shapes produced by different scattering particles: ice (FIG. 9A); volcanic ash (FIG. 9B); and smoke (FIG. 9C).
Figure 9B:
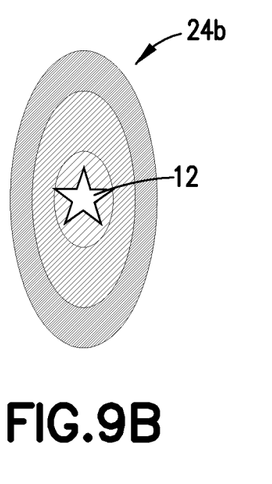
Figure 9C:
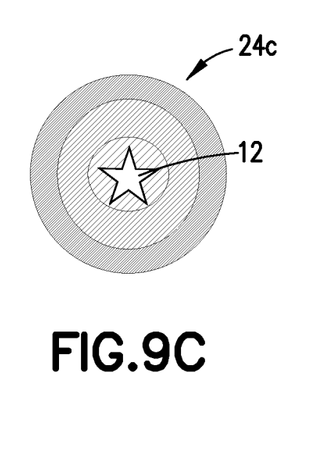

As depicted in FIGS. 9A through 9C, when viewed at low elevation angle, different scattering particles produce different corona shapes. Ice crystals predominantly scatter light upward or downward. They produce "light pillars" (such as a light pillar having corona shape 24a shown in FIG. 9A) which may extend several degrees above and below the apparent location of the sun, moon, or bright stars. Volcanic ash, with its high aspect ratio and horizontal orientation, also tends to scatter light upward or downward, but the many non-horizontal scattering surfaces scatter a large fraction of the light horizontally as well. The result is an elliptical corona 24b (see FIG. 9B). Smoke scatters light almost equally in all directions, so it produces a circular corona 24c (see FIG. 9C).

A corona from a star-like object is usually faint and may require a long exposure to detect. In some embodiments, the system (refer to FIG. 1) uses a long exposure time in the camera 4, or combines measurements from multiple short exposures, to form an image of a corona around the light source 2. The computer system 6 analyzes the shape of the corona. If the corona has a vertical orientation with an aspect ratio in a range of about 1.3 to 2.0, the computer system 6 sends an alert activation signal to the alert device 8, which then issues a visible or audible warning indicating the presence of volcanic ash along the intended flight path.

Data Fusion and Prior Information

In accordance with further embodiments, evidence from multiple detection methodologies can be combined to produce a more reliable assessment of the possible presence of a volcanic plume in the flight path of an aircraft. A preferred embodiment also uses outside information, such as reports of a volcanic eruption, forecasts of probable plume location, forecasts of cirrus clouds or smoke plumes, and/or weather, to improve its assessments. For example, the computer system may incorporate this information into a Bayesian analysis by adjusting the prior probabilities of observing various features. If a plume of smoke from a large forest fire is known to be in the area at cruise altitude, the computer system increases the prior probability of observing unusual refraction, scintillation, dimming, color shift, and circular corona. On the other hand, if cirrus clouds are in the forecast, the computer system adjusts the prior probability of observing dimming, color shift, polarization change, and vertical corona. The benefit of combining evidence and incorporating offboard information is to reduce the chance of false positives and false negatives in detecting volcanic plumes. Bayesian analysis is only an example. Numerous methods to combine diverse types of data are known in the art.

By reducing the risk of an encounter with volcanic ash, and doing so with minimal cost and weight, the system disclosed above reduces the risk of accidents, expensive maintenance, or flight delays.

While volcanic plume detection systems have been described with reference to various embodiments, it will be understood by those skilled in the art that various changes may be made and equivalents may be substituted for elements thereof without departing from the scope of the claims set forth hereinafter. In addition, many modifications may be made to adapt the teachings herein to a particular situation without departing from the scope of the claims.

As used in the claims, the term "computer system" should be construed broadly to encompass a system having at least one computer or processor, and which may have multiple computers or processors that communicate through a network or bus. As used in the preceding sentence, the terms "computer" and "processor" both refer to devices having a processing unit (e.g., a central processing unit) and some form of memory (i.e., computer-readable medium) for storing a program which is readable by the processing unit.

The method claims set forth hereinafter should not be construed to require that the steps recited therein be performed in the order in which they are recited. Nor should they be construed to exclude any portions of two or more steps being performed concurrently or alternatingly.

The invention claimed is:

1. A system for detecting airborne volcanic ash comprising: an air vehicle, a camera mounted to said air vehicle that outputs image data representing captured images of a distant point-like light source, and a computer system in communication with said camera for receiving said image data, wherein said computer system is programmed to process the image data from said camera to determine whether the image data comprises at least one visual feature indicative of a volcanic plume-induced effect due to the presence of a volcanic plume in the space between the air vehicle and the distant point-like light source or not, wherein said camera is directed toward the distant point-like light source, and wherein the volcanic plume-induced effect comprises one or more of the following: change in refraction, scintillation, change in polarization, and corona shape.

2. The system as recited in claim 1, further comprising an alert device in communication with said computer system, wherein said computer system is further programmed to send an alert activation signal to said alert device in response to a determination that some image data is indicative of said volcanic plume-induced effect.

3. The system as recited in claim 1, wherein said computer system is disposed onboard said air vehicle.

4. The system as recited in claim 1, wherein said image data processing comprises:
obtaining a known position of the distant light source;
adjusting the known position for refraction caused by a normal density gradient of an atmosphere;
calculating an apparent position of the distant light source based on the location of the camera and the image data; and
comparing the apparent position to the adjusted known position.

5. The system as recited in claim 4, wherein said image data processing further comprises detecting characteristics of the image data which are indicative of volcanic plume-induced scintillation.

6. The system as recited in claim 1, wherein said image data processing comprises analyzing the image data to determine whether at least some of the image data is consistent with a dimming pattern over time which is indicative of volcanic plume-induced dimming.

7. The system as recited in claim 6, wherein said camera is a color camera and said image data processing further comprises determining whether the image data indicates dimming accompanied by a shift to bluer wavelengths.

8. The system as recited in claim 6, further comprising means for detecting the degree of vertical polarization, wherein said image data processing further comprises calculating a ratio of a degree of vertical polarization to an amount of dimming.

9. The system as recited in claim 1, wherein said image data processing comprises analyzing the image data to determine whether at least some of the image data is consistent with light from a corona having a vertical orientation with an aspect ratio in a specified range.

10. A method to detect airborne volcanic ash, comprising:
attaching a camera to an air vehicle;
flying the air vehicle to a location from which volcanic ash may be visible;
capturing image data for at least one image of a distant point-like light source using a camera;
analyzing the image data to determine whether at least some of the image data is indicative of a volcanic plume-induced effect due to the presence of a volcanic plume in a space between the air vehicle and the distant point-like light source using a computer system;
generating an alert activation signal in response to detecting at least one visual feature indicative of the presence of a volcanic plume in the space between the air vehicle and the distant point-like light source; and
issuing a visible or audible alert in response to generation of said alert activation signal,
wherein the volcanic-induced effect comprises one or more of the following: change in refraction, scintillation, change in polarization, and corona shape.

11. The method as recited in claim 10, wherein said analyzing comprises:
obtaining a known position of the distant light source;
adjusting the known position for refraction caused by a normal density gradient of an atmosphere;
calculating an apparent position of the distant light source based on the location of the camera and the image data; and
comparing the apparent position to the adjusted known position.

12. The method as recited in claim 11, wherein said analyzing further comprises detecting characteristics of the image data which are indicative of scintillation.

13. The method as recited in claim 10, wherein said analyzing comprises analyzing the image data to determine whether at least some of the image data is consistent with a dimming pattern over time which is indicative of volcanic plume-induced dimming.

14. The method as recited in claim 13, wherein the camera is a color camera and said analyzing further comprises determining whether the image data indicates dimming accompanied by a shift to bluer wavelengths.

15. The method as recited in claim 13, wherein said analyzing further comprises calculating a ratio of a degree of vertical polarization to an amount of dimming.

16. The method as recited in claim 10, wherein said analyzing comprises determining whether at least some of the image data is consistent with light from a corona having a vertical orientation with an aspect ratio in a specified range.

17. A system for detecting airborne volcanic ash comprising:
an air vehicle;
a camera carried by the air vehicle, said camera outputting image data representing captured images of a distant point-like light source;
a computer system disposed onboard said air vehicle and in communication with said camera for receiving said image data, wherein said computer system is programmed to process the image data from said camera to determine whether at least some of the image data is indicative of volcanic plume-induced effect due to the presence of a volcanic plume in the space between the air vehicle and the distant point-like light source or not; and an alert device in communication with said computer system, wherein said computer system is further programmed to send an alert activation signal to said alert device in response to a determination that said image data comprises at least one visual feature indicative of the presence of a volcanic plume in the space between the air vehicle and the distant point-like light source, and wherein the volcanic plume-induced effect comprises one or more of the following: change in refraction, scintillation, change in polarization, and corona shape.

* * * * *